United States Patent
Hor-Lao et al.

(10) Patent No.: US 12,288,605 B2
(45) Date of Patent: Apr. 29, 2025

(54) ADAPTIVE CONTEXT SENSITIVE TIME DIVISION MULTIPLEXED CONTROL OF A HIGH FREQUENCY ABLATION DEVICE

(71) Applicant: Advanced Neuromodulation Systems, Inc., Plano, TX (US)

(72) Inventors: Mary Khun Hor-Lao, Prosper, TX (US); Binesh Balasingh, Prosper, TX (US); Scott DeBates, Frisco, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 1001 days.

(21) Appl. No.: 17/338,460

(22) Filed: Jun. 3, 2021

(65) Prior Publication Data

US 2022/0180999 A1 Jun. 9, 2022

Related U.S. Application Data

(60) Provisional application No. 63/123,212, filed on Dec. 9, 2020.

(51) Int. Cl.
*G16H 20/40* (2018.01)
*A61B 18/00* (2006.01)
*A61B 18/12* (2006.01)
*G16H 40/60* (2018.01)

(52) U.S. Cl.
CPC ......... *G16H 20/40* (2018.01); *A61B 18/1206* (2013.01); *G16H 40/60* (2018.01); *A61B 2018/00577* (2013.01); *A61B 2018/00761* (2013.01); *A61B 2018/124* (2013.01)

(58) Field of Classification Search
CPC ... H04B 1/40; A61B 18/1233; A61B 18/1206; A61B 2018/00577; A61B 2018/00761; A61B 2018/124; A61B 2018/00678; A61B 2018/00791; A61B 2018/00827; A61B 2018/00892; G16H 20/40; G16H 40/60
See application file for complete search history.

(56) References Cited

U.S. PATENT DOCUMENTS

| | | | |
|---|---|---|---|
| 7,736,357 B2 | 6/2010 | Lee, Jr. et al. | |
| 7,801,207 B2* | 9/2010 | Chen | H04B 1/40 |
| | | | 375/229 |
| 8,560,062 B2 | 10/2013 | Rittman, III et al. | |
| 10,342,606 B2 | 7/2019 | Cosman et al. | |

(Continued)

*Primary Examiner* — Eric C Wai
(74) *Attorney, Agent, or Firm* — Norton Rose Fulbright US LLP

(57) ABSTRACT

Implementations for adaptive context sensitive time division multiplexed scheduling and execution of tasks to be performed by a high frequency ablation system, such as an RF ablation system, are disclosed. The implementations may be effectuated in software, firmware, or both. Tasks may be categorized into categories corresponding to task priorities. Time blocks may be allocated during which execution of the tasks may be performed. The time blocks may be divided into time slots. A task may be assigned to a time slot based, at least in part, on a categorization priority of the task. Additionally, each task may be executed according to the schedule delineated by the time slots. An assignment of tasks to time slots may be adjusted based, at least in part, on data received at a high frequency ablation device of the high frequency ablation system.

14 Claims, 7 Drawing Sheets

(56) References Cited

U.S. PATENT DOCUMENTS

| | | | |
|---|---|---|---|
| 2008/0051777 A1* | 2/2008 | Haemmerich | A61B 18/1233 606/33 |
| 2009/0138011 A1* | 5/2009 | Epstein | A61B 18/1233 606/42 |
| 2013/0197510 A1 | 8/2013 | Heckel | |
| 2016/0081740 A1 | 3/2016 | Heckel et al. | |

* cited by examiner

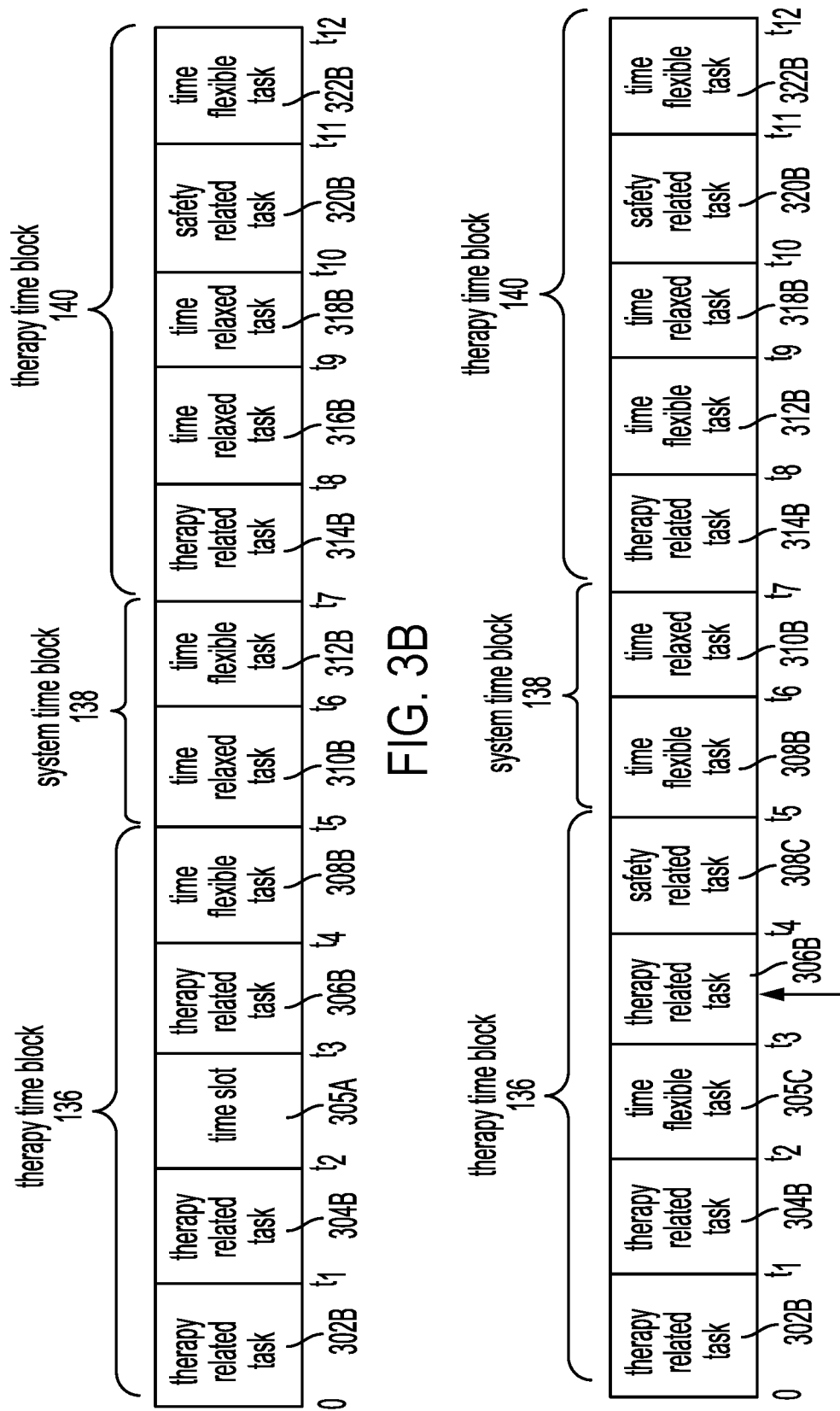

ADAPTIVE CONTEXT SENSITIVE TIME DIVISION MULTIPLEXED CONTROL OF A HIGH FREQUENCY ABLATION DEVICE

CROSS-REFERENCE TO RELATED APPLICATION

The present application claims the benefit of U.S. Provisional Patent Application No. 63/123,212 filed Dec. 9, 2020 and entitled "ADAPTIVE CONTEXT SENSITIVE TIME DIVISION MULTIPLEXED CONTROL OF A HIGH FREQUENCY ABLATION DEVICE," the disclosure of which is incorporated by reference in its entirety.

TECHNICAL FIELD

Aspects of the present disclosure relate generally to high frequency ablation systems and, more particularly, to time division multiplexed control of high frequency ablation systems.

BACKGROUND

Radiofrequency (RF) ablation is a medical therapy that is employed to treat a number of patient disorders. For example, RF frequency nerve ablation may be used to treat osteoarthritic pain of the spine through the destruction of nerves using RF energy. In an RF ablation system, an RF generator typically provides RF energy to one or more electrodes to ablate neural tissue where the electrodes are positioned using cannulas to access the target site. In addition to the RF generator, RF ablation systems may include various components, such as power electronics, sensors, peripheral devices including user interfaces, cooling systems, and sensors.

During therapy sessions, the RF ablation system generally monitors various therapy related parameters, such as a temperature at the one or more cannulas, to avoid damage to tissue surrounding nerves targeted by the ablation therapy while controlling the delivery of RF energy to the one or more cannulas. Further, while therapy related parameters are monitored and while delivery of RF energy is being regulated, the RF ablation system usually monitors system related parameters, such as user interfaces and a temperature within the RF ablation system itself. RF ablation systems traditionally employ hardware components to control and monitor the delivery of RF energy to the one or more cannulas and to monitor and control therapy related parameters and system related parameters.

SUMMARY

Disclosed are implementations for time division multiplexed scheduling and execution of tasks to be performed by a high frequency ablation system, such as a radiofrequency (RF) ablation system. Embodiments of an ablation system may, for example, provide adaptive context sensitive time division multiplexed control of high frequency ablation.

The high frequency ablation system of embodiments may include a first processor configured to execute therapy related tasks, such as delivery of RF energy to a patient, and safety related tasks, such as adjusting high frequency ablation therapy parameters. The first processor further may be configured to execute system related tasks, such as monitoring an operational integrity of the high frequency ablation system. The high frequency ablation system of embodiments may also include a second processor configured to execute input-output related tasks, such as responding to inputs received at one or more user interfaces of the high frequency ablation system and generating outputs at the one or more user interfaces.

In accordance with some aspects of the invention, one or more processors of a high frequency ablation system, (e.g., a first processor, a second processor, or both) may be configured to receive first data indicative of a type and quantity of hardware components associated with the high frequency ablation system, such as whether the high frequency ablation system includes a ground pad. Additionally or alternatively, the first processor, the second processor, or both may be configured to receive second data indicative of an operational state of the high frequency ablation system, such as a polarity of operation of the system, a state of therapy delivery (such as delivery of stimulation based therapy or ablation-based therapy), or both.

One or more processors of a high frequency ablation system of embodiments (e.g., a first processor, a second processor, or both) may be configured to allocate one or more time blocks (referred to herein as RF context time blocks) to scheduling therapy related tasks and safety related tasks in a time division multiplexed manner based on various data (e.g., the above mentioned first data, second data, or both). Additionally or alternatively, one or more time blocks (referred to herein as system context time blocks) may be allocated to scheduling system related tasks including input-output related tasks in the time division multiplexed manner. The first processor, the second processor, or both may be configured to further divide one or more RF context time blocks into one or more time slots during which particular therapy related tasks, also referred to as RF tasks or safety related tasks, may be scheduled for execution. Further, the first processor, the second processor, or both may be configured to divide one or more system context time blocks into one or more time slots during which particular system related tasks, input-output related tasks, or both may be scheduled for execution.

According to some embodiments of a high frequency ablation system, one or more processors (e.g., a first processor, a second processor, or both) may additionally or alternatively be configured to categorize tasks into a plurality of categories. The plurality of categories may include a time bound tasks category, having a first priority, a time flexible tasks category having a second priority, and a time relaxed tasks category having a third priority, wherein the first priority is higher than the second priority and the second priority is higher than the third priority. Tasks categorized into the time bound tasks category may include therapy related tasks, safety related tasks, or both. Tasks categorized into the time flexible tasks category may include system related tasks, and tasks categorized into the time relaxed tasks category may include input and output related tasks. In embodiments, tasks can be classified into the aforementioned categories based on static task characteristics, dynamic task characteristics, or both. An example of a static task characteristic may include an instruction to toggle one or more relays, indicative of a therapy-related task, which generally would be classified into a time bound task category. An example of a dynamic task characteristic may include receipt of data from one or more sensors, such as a thermocouple, indicating temperature variations, which, depending on a magnitude of the variation, may correspond to a time flexible task category.

Therapy related tasks may be scheduled for execution during particular and periodic time slots within the first one or more time blocks to facilitate multi-channel delivery of high frequency (RF) ablation therapy. Additionally or alternatively, time flexible tasks, time relaxed tasks, or both may be scheduled during time slots allocated to the first one or more time blocks in response to determining, for example, that time slots in the first one or more time blocks lack scheduled tasks and that time bound tasks are not pending in a time bound task scheduling queue for scheduling. One or more tasks may be rescheduled, such as in response to detecting an occurrence of an event or condition, such as an error in the operation of the high frequency ablation system, according to some aspects of the invention. Tasks other than therapy related tasks, such as system related tasks, may be scheduled during time blocks of varying periodicity.

The disclosed implementations confer numerous advantages. For example, by bifurcating execution of tasks between the first processor and the second processor according to some embodiments, an overall responsiveness of a high frequency ablation system may be enhanced. As another example, performing a multiplexed scheduling operation in software, firmware, or both according to some aspects of the disclosure may enhance an upgradability, adaptability, and a flexibility of a high frequency ablation system. In still another example, by categorizing tasks and prioritizing task categories in accordance with some embodiments, a balance can be achieved between real time control of therapy related tasks, such as high frequency ablation applied to a patient, and responsiveness to inputs received from one or more user interfaces. Deterministically allocating time slots to therapy related tasks, as provided according to some aspects of the invention, may reduce computational resources allocated to control of high frequency ablation therapy (e.g., RF ablation therapy) delivery to a patient, thereby liberating computational resources for other functions. In another example, dynamic task scheduling of embodiments may permit a high frequency ablation system to adapt to changed conditions, such as an error condition, thereby enhancing a safety of the high frequency ablation system.

Accordingly, in one aspect of the disclosure, a method of operating a high frequency ablation device that is configured to provide an ablation therapy to a patient is disclosed. The method may include operating a high frequency generator to generate a high frequency signal. Additionally, the method may include performing switching operations to output the high frequency signal to one or more output channels using time division multiplexing. The time division multiplexing may include operating the one or more processors to categorize multiple system tasks into a plurality of categories. The plurality of categories may include a time bound tasks category, having a first priority, a time flexible tasks category having a second priority, and a time relaxed tasks category having a third priority in which the first priority is higher than the second priority and the second priority is higher than the third priority. Further, the time division multiplexing may include operating the one or more processors to allocate, from a time block in which the tasks are to be scheduled, at least first one or more time blocks. Additionally, the time division multiplexing may include operating the one or more processors to divide the at least first one or more time blocks into one or more first time slots based, at least in part, on data corresponding to a state of a high frequency ablation system of which the high frequency ablation device is a component. Moreover, the time division multiplexing may include operating the one or more processors to schedule, in the one more first time slots, one or more time bound tasks corresponding to the time bound tasks category.

In an additional aspect of the disclosure, a high frequency ablation device for effectuating pain treatment through a time division multiplexing of tasks is disclosed. The high frequency ablation device may include a high frequency generator configured to generate a high frequency signal, one or more sensors, and switching components configured to control output the high frequency signal to one or more output channels. Additionally, the high frequency ablation device may include one or more processors coupled to the high frequency generator, the one or more sensors, and the switching components. The high frequency ablation device may further include a memory coupled to the one or more processors and configured to store instructions, which, when executed by the one or more processors, cause the one or more processors to categorize tasks into a plurality of categories. The plurality of categories may include a time bound tasks category, having a first priority, a time flexible tasks category having a second priority, and a time relaxed tasks category having a third priority, in which the first priority is higher than the second priority and the second priority is higher than the third priority. Additionally, the instructions, which, when executed by the one or more processors, may cause the one or more processors to allocate, from a time block in which the tasks are to be scheduled, at least first one or more time blocks, second one or more time blocks, or both. Further, the instructions, which, when executed by the one or more processors, may cause the one or more processors to divide the at least first one or more time blocks into one or more first time slots based, at least in part, on data corresponding to a state of the high frequency ablation system of which the high frequency ablation device is a component. Moreover, the instructions, which, when executed by the one or more processors, may cause the one or more processors to divide the second one or more time blocks into second one or more time slots based, at least in part, on the data. Additionally, the instructions, which, when executed by the one or more processors, may cause the one or more processors to schedule, in the one more first time slots, one or more time bound tasks and, in the one or more second time slots, one or more time flexible tasks, one or more time relaxed tasks, or both.

In yet an additional aspect of the disclosure, a non-transitory computer-readable medium for storing instructions is disclosed, that, when executed by one or more processors of a high frequency ablation device, is configured to provide an ablation therapy to a patient. The instructions, which, when executed by the one or more processors, may be configured to operate a high frequency generator to generate a high frequency signal. Additionally, the instructions, which, when executed by the one or more processors, may be configured to perform switching operations to output the high frequency signal to one or more output channels using time division multiplexing. The time division multiplexing may include operating the one or more processors to categorize the tasks into a plurality of categories. The plurality of categories may include a time bound tasks category, having a first priority, a time flexible tasks category having a second priority, and a time relaxed tasks category having a third priority, in which the first priority is higher than the second priority and the second priority is higher than the third priority. Additionally, time division multiplexing may include operating the one or more processors to allocate, from a time block in which the tasks are to be scheduled, at least first one or more time blocks. Further, the time division multiplexing may include operating the one or more processors to divide the at least first one or more time blocks into one or more first time slots based, at least in part, on data corresponding to a state of the high frequency ablation system of which the high frequency ablation device is a component. Moreover, the time division multiplexing may include operating the one or more processors to schedule, in the one more first time slots, one or more time bound tasks corresponding to the time bound tasks category.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

FIGS. 3A, 3B, and 3C are block diagrams illustrating an example adaptive context sensitive time division multiplexed scheduling operation according to one or more aspects;

DETAILED DESCRIPTION

Figure 1:
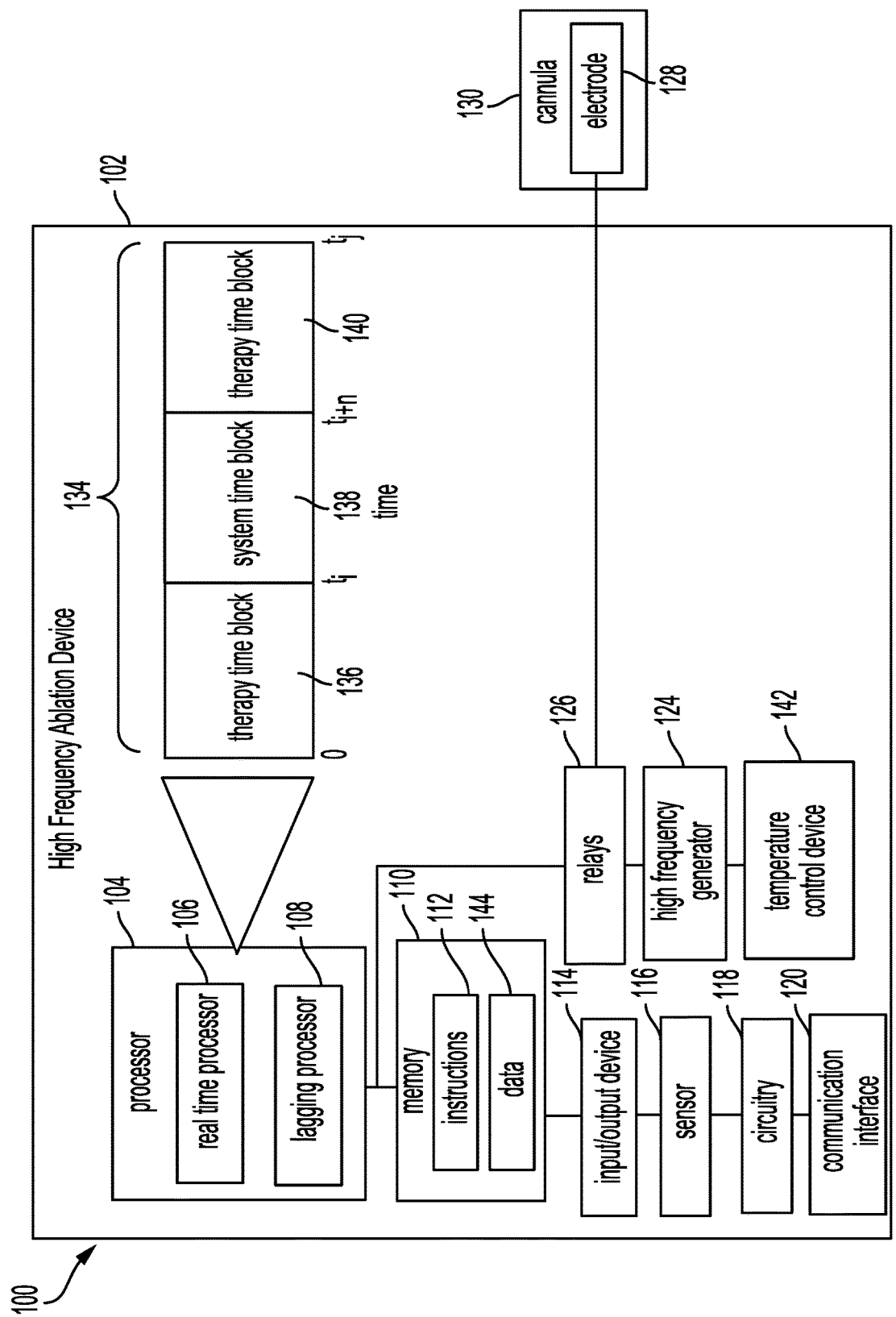
FIG. 1 is a block diagram illustrating details of an example high frequency ablation system according to one or more aspects.

FIG. 1 is a block diagram illustrating details of an example high frequency ablation system 100 according to one or more aspects. High frequency ablation system 100 may, for example, be used to ablate neural tissue of a patient to treat chronic pain. By scheduling and executing multiple tasks, such as hundreds of thousands or millions of tasks, within a short timeframe, such as milliseconds, components of high frequency ablation system 100 may provide high frequency (e.g., radiofrequency (RF)) ablation therapy to the patient, while monitoring a physical integrity of the system itself and responding to user inputs.

High frequency ablation system 100 of the illustrated embodiment includes high frequency ablation device 102, one or more electrodes 128 (hereinafter referred to collectively as "electrode 128"), and one or more cannulas 130 (hereinafter referred to collectively as "cannula 130"). High frequency ablation device 102 may be coupled to electrode 128 wirelessly or through wires. Electrode 128 may be coupled to cannula 130. Cannula 130 may be configured to be coupled to a patient, by for example, insertion of cannula 130 into the patient's body to position electrode 128 in proximity of neural tissue for ablation. Electrode 128 may be inserted within a patient's body through cannula 130 as illustrated in FIG. 1. Electrode 128 may also be implemented in a manner where electrode 128 is physically integrated with cannula 130. Other ablation probe devices with one or more electrodes 128 may be employed according to some embodiments.

In an implementation, high frequency ablation device 102 may be an RF ablation device. Embodiments of a high frequency ablation device may include one or more processors. Accordingly, high frequency ablation device 102 of the illustrated embodiment is shown as including real time processor 106 and lagging processor 108 (referred to collectively as "processor 104"). It should be appreciated, however, that various numbers and configurations of processors may be provided in implementations of a high frequency ablation device operable in accordance with concepts of the present disclosure. High frequency ablation device 102 is further shown as including memory 110, such as may be used to store instructions and/or data utilized by processor 104 of embodiments. Additionally, high frequency ablation device 102 includes one or more input/output devices 114 (hereinafter referred to collectively as "input/output device 114"), one or more sensors 116 (hereinafter referred to collectively as "sensor 116"), circuitry 118, and communication interface 120. Further, high frequency ablation device 102 includes one or more relays or switching circuitry 126 (hereinafter referred to collectively as "relays 126") configured to be coupled to electrode 128. Moreover, high frequency ablation device 102 includes high frequency generator 124, which may be an RF generator, and temperature control device 142.

Processor 104 (e.g., real time processor 106) may be configured to execute therapy related tasks, such as delivery of high frequency energy (e.g., RF energy) to a patient, and safety related tasks, such as adjusting high frequency ablation therapy parameters of a high frequency ablation therapy. Processor 104 (e.g., real time processor 106) further may be configured to execute system related tasks, such as monitoring an operational integrity of high frequency ablation system 100. Additionally or alternatively, processor 104 (e.g., lagging processor 108) may be configured to execute input output related tasks, such as responding to inputs received at input/output device 114, generating an output at input/output device 114, or both. Processor 104 may comprise one or more microprocessors, graphical processing units (GPUs), field programmable gate arrays (FPGAs), microcontrollers, application specific integrated circuits (ASICs), and/or other logic circuitry configured to perform the operations described herein (e.g., operations described with reference to FIGS. 1, 2, 3A-3C, 4A-4B, 5A-5B), or any combination thereof.

Memory 110 of embodiments may be a non-transitory computer-readable medium configured to store instructions, such as instructions 112 (e.g., software, firmware, etc.), and/or data 144 utilized by processor 104 and/or other components of high frequency ablation device 102. Memory 110 may include a random access memory (RAM), which can be synchronous RAM (SRAM), dynamic RAM (DRAM), synchronous dynamic RAM (SDRAM), or the like. Memory 110 may additionally or alternatively include read only memory (ROM), which can be programmable read only member (PROM), erasable programmable read only member (EPROM), electrically erasable programmable read only memory (EEPROM), optical storage, or the like. Additionally or alternatively, memory 110 may include hard disk drives (HDDs), solid state disk drives (SSDs), and other memory devices configured to store data, instructions, or both in a persistent or a non-persistent state. Memory 110 may be coupled to processor 104 and/or other components of high frequency ablation device 102.

When executed by processor 104, instructions 112 or some portion thereof may cause processor 104 to perform operations. These operations may include adaptive context sensitive time division multiplexing operations, examples of which are described more fully with reference to FIGS. 1, 2, 3A-3C, 4A-4B, 5A-5B, or any combination thereof. Instructions 112 may, for example, comprise software, firmware, or a combination thereof.

Input/output device 114 may be configured to receive one or more inputs from a user of high frequency ablation system 100, to generate one or more outputs for the user of the high frequency ablation system 100, or both. Input/output device 114 may include a keyboard, a mouse, a joystick, a touch-sensitive display, and/or other user interfaces, or any combination thereof. Additionally or alternatively, input/output device 114 may include a speaker. In an implementation, input/output device 114 may be configured to render a graphical user interface (GUI) to receive inputs from and to render outputs for the user of high frequency ablation system 100.

Sensor 116 may be configured to receive a signal, monitor or detect a parameter, generate a digital, analog, and/or mixed signal output, or any combination thereof. In an implementation, sensor 116 may include a thermocouple, a tachometer, a voltmeter, an ammeter, or any combination thereof. Although depicted as being positioned within high frequency ablation device 102, sensor 116 also be positioned within cannula 130. Sensor 116 may be coupled to processor 104 and/or other components of high frequency ablation device 102. Sensor 116 may be configured to provide multiple inputs to processor 104 in parallel. For example, a thermocouple corresponding to sensor 116 may be configured to provide first input data to processor 104 simultaneously with second input data provided to processor 104 by a voltmeter. The one or more sensors (e.g., sensor 116) may correspond to one or more input channels through which data is provided to processor 104.

Temperature control device 142 may be configured to cool components of high frequency ablation device 102. As an example, temperature control device 142 may be a fan, a thermoelectric cooler, passive cooling material, etc. Temperature control device 142 may, for example, be coupled to processor 104, to sensor 116, or to both and/or other components of high frequency ablation device 102.

Circuitry 118 may include various analog, digital, or mixed signal electronics configured to regulate an output voltage generated by high frequency generator 124. As configured to regulate an output voltage according to some examples, circuitry 118 may include a subtractor circuit configured to calculate a temperature error as a difference between a target temperature and a measured temperature at a tip of cannula 130, a proportional-integral-derivative (PID) controller coupled to the subtractor circuit and configured to apply a high frequency voltage, such as an RF voltage, to the tip of cannula 130, the PID controller configured to determine the high frequency voltage based on the temperature error and a proportional coefficient, an integral coefficient, and a derivative coefficient of the PID controller. Circuitry 118 may further include a PID coefficient controller coupled to the PID controller, the PID coefficient controller configured to dynamically adjust the proportional, integral, and derivative coefficients of the PID controller during operation of high frequency ablation device 102. Circuitry 118 may be coupled to processor 104, to high frequency generator 124, or to both and/or other components of high frequency ablation device 102.

Communication interface 120 may be configured to receive and send data using a plurality of communication protocols, such as a Bluetooth™ protocol, a Zigbee™ protocol, a cellular communication protocol, such as any of the 3G, 4G, or 5G communication protocols, or any combination thereof. Communication interface 120 may, for example, comprise a network interface card (NIC), a transceiver, a transmitter, a receiver, or any combination thereof. Additionally or alternatively, communication interface 120 may comprise networking hardware capable of communicating using the 802.11 communication standard, the Ethernet communication standard, other communication standards that may be developed, or any combination thereof. Communication interface 120 may be coupled to processor 104 and/or other components of high frequency ablation device 102.

High frequency generator 124 may be configured to generate and provide high frequency energy, such as RF energy, via electrode 128. In an implementation, high frequency generator 124 may be an RF generator. High frequency generator 124 may be coupled to relays or switching circuitry (hereinafter "relays 126"), which, in turn, may be coupled to electrode 128. Relays 126 may comprise suitable components to controllably connect the output from high frequency generator 124 to one or more output channels. In some implementations, relays 126 may be implemented using mechanical switches to connect the RF signal from high frequency generator 124 to selected output channels. In some embodiments, relays 126 may be one or more switches such as, for example, one or more transistors, configured to selectively connect the output signal from high frequency generator 124 to one or more output channels for the respective electrodes 128 such that multi-channel high frequency ablation therapy, such as RF ablation therapy, may be provided to a patient. The selected output channels may be changed during a therapy session according to time division multiplexing as discussed herein. For example, in implementations, the one or more electrodes (e.g., electrode 128) may correspond to one or more channels for multi-channel delivery of high frequency ablation therapy to a patient. Additionally, high frequency generator 124 may be coupled to processor 104 and/or other components of high frequency ablation device 102.

Although FIG. 1 depicts independent hardware blocks capable of providing inputs, such as sensory inputs to the one or more processors simultaneously, and/or capable of providing outputs, such as RF energy outputs, simultaneously, in an embodiment, a single hardware block implementing the functionalities described with respect to FIGS. 1-5B may be deployed. In an embodiment utilizing a single hardware block with multiple functionalities, one or more muxes, for example, may be used to switch among the functionalities, thereby effectuating multi-channel operation.

During operation of high frequency ablation system 100, processor 104 may receive first data indicative of a physical state of high frequency ablation system 100, second data indicative of an operational state of high frequency ablation system 100, or both. Data 144 may include the first data, the second data, or both. The physical state of high frequency ablation system 100 may correspond to a type and a quantity of components of high frequency ablation system 100. For example, the physical state of high frequency ablation system 100 may correspond to a quantity of electrodes, such as electrode 128, and cannulas, such as cannula 130, coupled to high frequency ablation device 102, whether high frequency ablation device 102 includes a ground pad, a configuration of one or more electrodes, such as electrode 128, of high frequency ablation system 100, or any of the foregoing. The operational state of high frequency ablation system 100 may correspond to a polarity of operation of high frequency ablation system 100, a state of therapy delivery (such as delivery of stimulation based therapy or ablation-based therapy), or both. As another example, the operational state of high frequency ablation system 100 may correspond to a condition that may sporadically arise with respect to high frequency ablation system 100, such as an error state of high frequency ablation system 100.

Based, at least in part, on the first data, the second data, or both, instructions 112 may be configured to cause processor 104 to allocate time block 134, corresponding to a time in which high frequency ablation system 100 is configured to perform one or more tasks, into first one or more time blocks, depicted in FIG. 1 as therapy time blocks 136, 140, second one or more time blocks, depicted in FIG. 1 as system time block 138, or both. A task may include, as examples, an ablation pulse, an instruction to read data generated at a sensor, such as sensor 116, an instruction sent to circuitry, such as circuitry 118, to initiate a PID loop, and the like. Although two therapy time blocks 136, 140 and one system time block 138 are depicted in FIG. 1, any number of therapy time blocks, system time blocks, or both can be allocated to accommodate multi-channel task scheduling.

In an implementation, instructions 112 may be configured to cause processor 104 to initially schedule therapy related tasks and safety related tasks within therapy time blocks 136, 140 and system related tasks, including input-output related tasks, within system time block 138. In implementations, after initially scheduling therapy related tasks and/or safety related tasks within therapy time blocks 136, 140, instructions 112 may be configured to cause processor 104 to schedule system related tasks within therapy time blocks 136, 140 in response to determining, for example, that time slots are available for scheduling tasks within therapy time blocks 136, 140 and that therapy related tasks and/or safety related tasks are not pending scheduling (in one or more scheduling queues). In embodiments, therapy time blocks, such as therapy time blocks 136, 140, may occur with fixed periodicities, while system time blocks, such as system time block 136 may occur with variable periodicities.

Therapy related tasks of embodiments may, for example, include tasks associated with providing ablation therapy to a patient. For instance, therapy related tasks may include controlling relays 126 to a selected channel configuration, setting a level of an output voltage generated at high frequency generator 124, measuring a level of a current output at electrode 128, measuring a temperature at a thermocouple positioned within cannula 130 that may be indicative of a temperature of tissue surrounding electrode 128, or any combination thereof. Safety related tasks of embodiments may, for example, include checking that a position of electrode 128 has not shifted, checking that high frequency ablation system 100 has no electrical shorts to ground, or combinations thereof. System related tasks of embodiments may, for example, include monitoring a performance of the high frequency ablation device 102 during a therapy session, such as checking a temperature within a housing of high frequency ablation device 102, sending instructions to temperature control device 142 to regulate a temperature within a housing of high frequency ablation device, or any combination thereof.

Figure 3A:
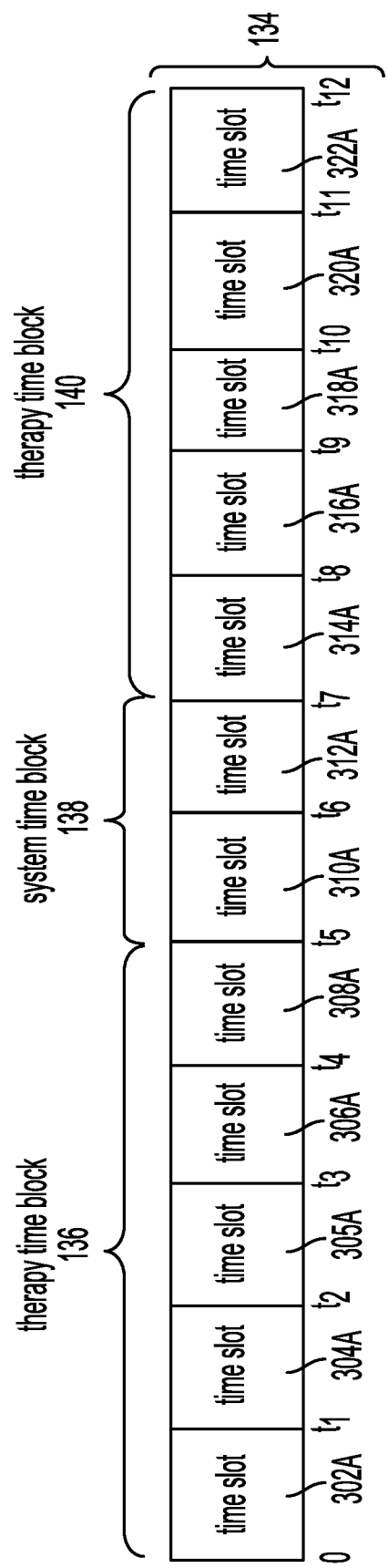

Referring to FIG. 3A, instructions 112 may further be configured to cause processor 104 to divide first one or more time blocks, such as therapy time blocks 136, 140, into one or more time slots, such as time slots 302A-308A and 314A-322A, respectively, during which particular therapy related tasks or safety related tasks may be scheduled for execution. Additionally or alternatively, referring to FIG. 3A, instructions 112 may further be configured to cause processor 104 to divide the second one or more time blocks, such as system time block 138, into one or more time slots, such as time slots 310A, 312A, during which particular system related tasks, input output related tasks, or both may be scheduled for execution. It is understood that the number of time slots depicted in FIG. 3A is for illustrative purposes only and that any arbitrary number of time slots can be scheduled within time blocks.

Figure 2:
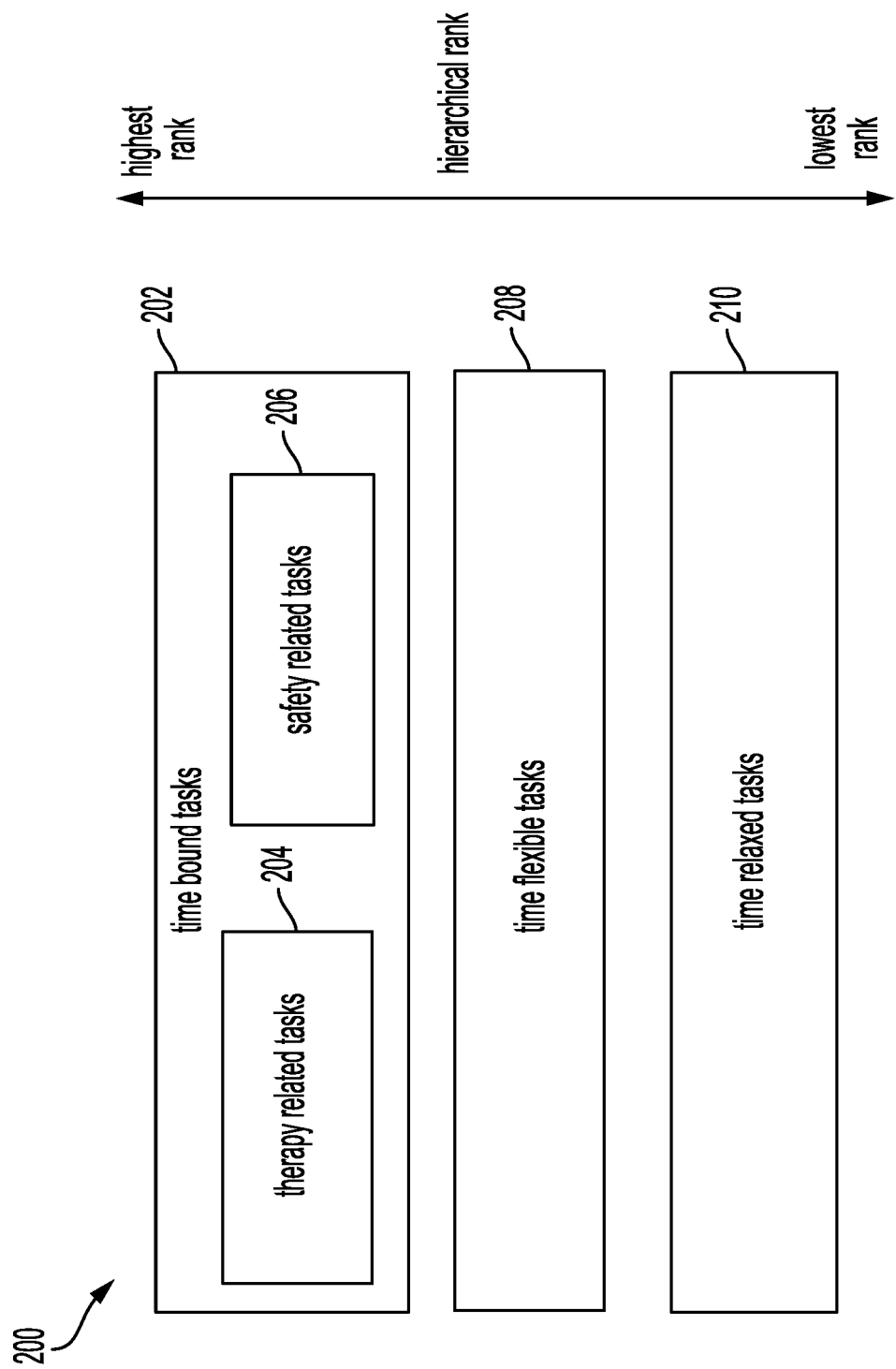
FIG. 2 is a block diagram illustrating details of an example task categorization paradigm according to one or more aspects.

Additionally and with reference to FIG. 2, instructions 112 may further be configured to cause processor 104 to categorize tasks into time bound tasks 202, time flexible tasks 208, and/or time relaxed tasks 210. Time bound tasks 202 may, for example, include tasks that, ideally, are to be performed within a specified timeframe, such as may comprise therapy related tasks, safety related tasks, or both according to some embodiments. Time flexible tasks 208 of examples may include tasks that may be performed within different timeframes, such as may comprise system related tasks according to some embodiments. Time relaxed tasks 210 may, for example, include tasks that may be executed within any timeframe, such as may comprise input-output related tasks according to some embodiments. According to some implementations, time bound tasks 202 have a higher scheduling or execution priority than time flexible tasks 208 and/or time flexible tasks have a higher scheduling or execution priority than time relaxed tasks 210.

Instructions 112 may additionally or alternatively be configured to cause processor 104 to schedule tasks during particular time slots based on a context of the task, such as whether a task is a time bound task (e.g., a therapy related task, a safety related task), a time flexible tasks (e.g., a system related task), a time relaxed task (e.g., an input/output related task), or other context dependent parameters that may relate to task priority, such as receiving sensory inputs from one or more sensors (e.g., sensor 116 of FIG. 1) that are indicative of an error condition (e.g., sharp temperature variations sampled at one or more thermocouples of high frequency ablation device 100 of FIG. 1). Thus, instructions 112 may implement context sensitive time division multiplexed scheduling of tasks. For example, and with reference to FIG. 3B, processor 104 may be configured to schedule therapy related tasks, such as therapy related tasks 302B and 306B, during particular and periodic time slots within the first one or more time blocks to, for instance, facilitate multi-channel delivery of high frequency (RF) ablation therapy. As another example of scheduling tasks during particular time slots and with reference to FIG. 3B, processor 104 may be configured to schedule time relaxed task 310B and time flexible task 312B during time slots within system time block 138.

In accordance with some embodiments, instructions 112 may be configured to cause processor 104 to adaptively reschedule tasks. For example and referring to FIGS. 3B and 3C, in response to detecting error event 342C indicative of a potential safety problem, such as a displacement of electrode 128, instructions 112 may configure processor 104 to schedule a safety related task, such as safety related task 308C, within time slot 308A during which time flexible task 308B had been scheduled prior to occurrence of error event 342C. Processor 104 may be further configured to reschedule tasks occurring subsequent to error event 342C by, for instance, scheduling time flexible task 308B to occur at a time slot during which time relaxed task 310B had been scheduled to occur prior to the occurrence of error event 342C.

Additionally or alternatively, instructions 112 of embodiments may be configured to cause processor 104 to adaptively schedule tasks. For instance and referring to FIGS. 3B and 3C, in response to determining that a therapy related task has not been scheduled for time slot 305A and that no therapy related tasks are pending scheduling in, for instance, a time bound task scheduling queue, processor 104 may be configured to schedule time flexible task 305C in therapy time block 136 as depicted in FIG. 3C.

In an implementation, once tasks have been scheduled, instructions 112 of embodiments may be configured to cause real time processor 106 to execute one or more time bound tasks, such as therapy related tasks, safety related tasks, or both. Further, instructions 112 of embodiments may be configured to cause lagging processor 108 to execute one or more time flexible tasks, one or more time relaxed tasks, or both. In this manner, a responsiveness of inputs received an input/output device 114 may be balanced against real time control of therapy related tasks.

Instructions 112 that configure processor 104 to perform an adaptive context sensitive time division multiplexed control of high frequency ablation device 102 confer several advantages. For example, by performing a multiplexed scheduling operation in software, firmware, or both in accordance with concepts of the present disclosure, rather than through special purpose circuitry configured to implement the adaptive context sensitive time division multiplexed operations described herein, an upgradability, adaptability, and a flexibility of high frequency ablation system 100 may be enhanced. For instance, instructions 112 may be modified and upgraded more easily than in a special purpose hardware implementation of the logic corresponding to instructions 112. To illustrate, an enhanced or improved instruction set, such as an improvement to instructions 112, may be generated and provided to high frequency ablation device wirelessly via communication interface 120. In this manner, as more high frequency ablation devices (such as high frequency device 102) are deployed and as more data is generated from their use, instructions 112 may be updated to reflect improvements generated from data acquired from the more widespread deployment and use of the high frequency ablation devices.

As another example, by categorizing tasks and prioritizing task categories according to embodiments of the invention, a balance may be achieved between real time control of therapeutic tasks, such as high frequency ablation applied to a patient, and responsiveness to input/output devices 114, such as user interfaces. In still another example, deterministically allocating time blocks for therapy-related tasks in accordance with concepts of the present invention may reduce computational resources allocated to PID control of high frequency ablation therapy (e.g., RF ablation therapy) delivery to a patient, thereby liberating computational resources for other functions, such as enhancing a responsiveness of the high frequency ablation device 102 to user inputs received via input/output devices 114. By improving a responsiveness of high frequency ablation device 102, an experience of the device user, such as a clinician, is enhanced. Additionally or alternatively, by prioritizing time bound tasks over time flexible tasks and time relaxed tasks according to some embodiments, therapy related tasks and safety related tasks may be completed more rapidly while not sacrificing the operational integrity of high frequency ablation system 100. In this manner, an efficiency of therapy delivery may be enhanced, which may provide benefits to patients (e.g., less time in treatment) and to health care providers (e.g., more time available to treat other patients). As a further example, dynamic task scheduling implemented according to some aspects of the invention permits high frequency ablation system 100 to adapt to changed conditions, such as an error condition (e.g., a dislocated electrode), thereby enhancing a safety of high frequency ablation system 100.

Thus, high frequency ablation device 102 may be configured to schedule multiple tasks, such as hundreds of thousands or millions of tasks, within a short timeframe, such as in milliseconds or millionths of seconds. By scheduling a large number of tasks, multi-channel therapy can be provided at various positions within a patient's body, such as via a plurality of electrodes positioned in various parts of a patient's spine. Accordingly, implementations described herein may be configured to enhance an efficiency of high frequency ablation therapy.

FIG. 2 is a block diagram illustrating details of an example task categorization paradigm 200 according to one or more aspects. In task categorization paradigm 200, tasks are categorized into a first category that includes time bound tasks 202, a second category that includes time flexible tasks 208, and a third category that includes time relaxed tasks 210. The task categories of embodiments may include further categorization, such as to include sub-categories. For example, time bound tasks 202 of the illustrated first category is shown as including sub categories in which a first sub category includes therapy related tasks 204 and a second sub category includes safety related tasks 206. Tasks belonging to the first category may, for example, have a higher scheduling or execution priority than tasks that belong to the second category. Similarly, tasks belonging to the second category of embodiments may have a higher scheduling or execution priority than tasks belonging to the third category. In an implementation, tasks belonging to therapy related tasks 204 may have a higher priory than tasks belonging to safety related tasks 206. However, in other implementations, tasks belonging to safety related tasks 206 may have a higher priority than tasks belonging to therapy related tasks 204. In yet other implementations, tasks belonging to safety related tasks 206 may have the same priority as tasks belonging to therapy related tasks 204. Although tasks are described as being categorized into a first category, a second category, and/or a third category, other categories are possible.

Each task may correspond to a particular instruction to be executed by one or more processors of a high frequency ablation device, such as processor 104 of FIG. 1, or that one or more processors, such as processor 104 of FIG. 1, may cause a component of a high frequency ablation device, such as high frequency ablation device 102 of FIG. 1, to perform. In an implementation, instruction code corresponding to each task may include a header or other designation indicative of whether the task is a time bound task, a time flexible task, or a time relaxed task. If a task is a time bound task, instruction code corresponding to therapy related tasks may have a particular designation, such as an indicator included within the instruction code. Similarly, safety related tasks may have another particular designation or indicator included within the instruction code to indicate that the instruction corresponds to a safety related task.

Alternatively or additionally, a processor, such as processor 104, of a high frequency ablation system, such as high frequency ablation system 100, may categorize tasks as, for instance, time bound tasks, time flexible tasks, or time relaxed tasks, based on static task characteristics, dynamic task characteristics, or both. Static task characteristics may correspond to instructions to activate components of a high frequency ablation device, such as high frequency ablation device 100 of FIG. 1, that generally correspond to time bound tasks (e.g., therapy related tasks), time flexible tasks, or time relaxed tasks. For example, instructions to activate or operate components of the high frequency ablation device (e.g., high frequency ablation device 100 of FIG. 1) associated with delivery of RF energy, such as instructions to toggle relays (e.g., relays 126 of FIG. 1) into on/off or off/on states, generally correspond to therapy related tasks. Therefore, a processor (e.g., processor 104 of FIG. 1) of the high frequency ablation system (e.g., high frequency ablation system 100) would generally categorize the foregoing tasks as time bound tasks. As another example, tasks that correspond to instructions to activate temperature sensors (e.g., corresponding to sensor 116 of FIG. 1) that sense a temperature within a housing of the high frequency ablation system would generally be categorized by a processor of the high frequency ablation device as time flexible tasks. As an additional example, instructions to accept inputs from input/output devices (e.g., input/output device 114 of FIG. 1) of a high frequency ablation device may be categorized by the processor of the high frequency ablation system as time relaxed tasks.

Dynamic tasks characteristics may correspond to receipt of data from sensors (e.g., sensor 116 of FIG. 1), input/output devices (e.g., input/output device 114 of FIG. 1), and/or other components of the high frequency ablation device indicative of the task category. For example certain temperature variation data (e.g., corresponding to data 144 of FIG. 1) received from thermocouples indicative of temperature spikes in tissue surrounding the electrodes (e.g. electrode 128 of FIG. 1) of the high frequency ablation system may indicate that a time bound task, such as a safety related task to reduce or lower an output voltage provided to the electrode, might have to be scheduled. As another example, receipt of data from a temperature sensor within a housing of the high frequency ablation device indicative of rising temperature within the housing might trigger scheduling of an instruction to initiate a temperature control device (e.g., temperature control device 142 of FIG. 1) of the high frequency ablation device, which a processor of the high frequency ablation device generally would categorize as a time flexible task. A further example includes receipt of data from an input/output device (e.g., input/output device 114 of FIG. 1) of the high frequency ablation system indicative of a time relaxed task, such as an instruction to process input received from an input/output device of the high frequency ablation device.

FIGS. 3A-3C are block diagrams illustrating an example adaptive context sensitive multiplexed time division scheduling operation according to one or more aspects. A processor (e.g., one or more processors), such as processor 104 of FIG. 1, of a high frequency ablation device, such as high frequency ablation device 102 of FIG. 1, may be configured, based on instructions such as instructions 112 stored in a memory of the high frequency ablation device, to perform a time division multiplexing operation by dividing time block 134, in which tasks are to be scheduled, into one or more first time blocks, corresponding to therapy time blocks 136, 140. Therapy time blocks 136, 140 may be referred to as a radio frequency (RF) context, since the processor may be configured to principally schedule time bound tasks, such as therapy related tasks and/or safety related tasks, within therapy time blocks 136, 140. Further, therapy time blocks 136, 140 may collectively correspond to a high frequency (e.g., an RF) ablation cycle period during which high frequency ablation therapy is to be delivered to a patient.

Additionally or alternatively, the instructions may be configured to cause the processor to divide time block 134 into one or more second time blocks, corresponding to system time block 138. System time block 138 may be referred to as a system context, since the processor may be configured to schedule system related tasks within system time block 138. For example, the processor may be configured to schedule time relaxed tasks, time flexible tasks, or both in system time block 138. In some implementations, the one or more second time blocks, such as system time block 138, may be omitted such that time block 134 only includes therapy time blocks, such as therapy time block 136, 140.

In implementations, the RF context, the system context, or both may have a plurality of context layers. For example, in an implementation, the RF context may include a therapy task sub-context, a safety task sub-context, or both. Further, and as an example, the system context may include a time flexible task sub-context, a time relaxed task sub-context, or both. Although an RF context and a system context are described, other contexts are possible.

The instructions may further configure the processor to subdivide therapy time blocks 136, 140 and system time block 138 into one or more time slots, such as time slots 302A-322A of FIG. 3A. A time slot may correspond to a period of time during which a task assigned, by the processor, to the time slot is to be scheduled, executed, or both. The processor may be configured to perform the foregoing time division operation, for example, based on data, such as data 144 of FIG. 1, received by the processor and stored in a memory, such as memory 110 of FIG. 1.

In implementations, the data may include first data indicative of a physical state of a high frequency ablation system, such as high frequency ablation system 100 of FIG. 1, of which the high frequency ablation device is a component. The physical state of the high frequency ablation system may, for example, correspond to a number of electrodes, such as electrode 128, of the high frequency ablation system, a configuration of the electrodes, the absence or presence of a ground pad, a number and type of sensors of the high frequency ablation system, or any of the foregoing. Additionally or alternatively, the data may include second data indicative of an operational state of the high frequency ablation system. An operational state of the high frequency ablation system may, for example, correspond to a state of therapy delivery of the high frequency ablation system, such as whether the high frequency ablation system is configured to deliver stimulation therapy, impedance-based therapy, or high frequency (e.g., RF) ablation therapy.

In an implementation, a duration of each time slot may depend on various aspects (e.g., aspects of the first data, the second data, or both). For example, the processor may be configured to divide the one or more first time blocks (e.g., therapy time blocks 136. 140), the one or more second time blocks (e.g., system time block 138) or both into a set slot size. The processor then may be configured to increase or decrease the set slot size based, at least in part, on the various aspects. To illustrate, the processor may be configured to reduce a duration of each time slot, such as time slots 302A-322A of FIG. 3A, in response to determining that a first quantity of electrodes are coupled to the high frequency ablation device and to increase a duration of each time slot in response to determining that a second quantity of electrodes are coupled to the high frequency ablation device, where the second quantity is smaller than the first quantity. Additionally or alternatively, the processor may be configured to determine a duration of each time slot and may subsequently adjust the duration of each time slot based, at least in part, on the various aspects, such as aspects of the first data, the second data, or both.

As a further example of dynamic, context-aware time slot allocation, in response to providing a particular type of therapy, such as high frequency (e.g., RF) ablation therapy as opposed to stimulation therapy, the processor of the high frequency ablation device may be configured to allocate statically defined time slots to therapy-related tasks, such as toggling relays (e.g. relays 126 of FIG. 1) to deliver RF therapy to a patient via electrodes (e.g., electrode 128 of FIG. 1). In parallel, the processor may be configured to allocate time slots to non-therapy related tasks, such as receiving inputs from sensors, such as a thermocouple embedded within a housing of the high frequency ablation device to monitor a temperature within the housing of the high frequency ablation device while RF therapy is being delivered to a patient. In this manner, scheduling and execution of therapy-related tasks can be balanced against scheduling and execution of critical non-therapy related tasks.

The processor may be configured to schedule a task in a time slot as depicted in FIG. 3B in which, for example, therapy related task 302B is scheduled within time slot 302A and time relaxed task 310B is scheduled within time slot 310A. As an example, the processor may be configured to schedule time bound tasks, such as therapy related tasks 302B, 304B, 306B, and 314B during therapy time blocks 136, 140, respectively. The processor may be configured to schedule time flexible tasks, time relaxed tasks, or both during system time block 138.

In implementations, the instructions may be configured to cause the processor to schedule therapy related tasks during particular and periodic time slots of therapy time blocks. For instance and as illustrated in FIGS. 3A and 3B, the processor may be configured to schedule therapy related tasks 302B, 314B during the first time slots 302A, 314A in each respective therapy time block 136, 140. Scheduling therapy related tasks during particular time slots in a repeating pattern (e.g., periodically) may reduce a number of calculations to be performed by the processor during high frequency ablation therapy thereby enhancing an accuracy and a control of the therapy. To illustrate, by deterministically allocating time slots for therapy related tasks, a control loop (e.g., a proportional-integral-derivative (PID) control loop) does not need to compensate for time, thereby liberating computational resources of the high frequency ablation device to perform other tasks.

Further, in response to determining that that time slots are available in therapy time blocks 136, 140 because, for example, time bound tasks, such as therapy related tasks, safety related tasks, or both, are not pending scheduling in a scheduling queue, instructions may be configured to cause the processor to schedule time flexible tasks, such as time flexible task 308B, time relaxed tasks, such as time relaxed task 316B, or both in therapy time blocks 136, 140. In implementations, the processor may be configured to leave time slots, such as time slot 305A, unassigned so that tasks may subsequently be scheduled in the unassigned time slots.

Additionally or alternatively, in other implementations, the processor may be configured to reassign a lower priority task, such as time flexible tasks, time relaxed tasks, or both to other time slots, to replace a scheduled lower priority task, such as a time flexible task, with a higher priority task, such as a safety related task, or any combination thereof.

Referring to FIG. 3C, the processor may be configured to dynamically and adaptively reschedule tasks in response to the occurrence of an event or condition, such as the occurrence of error event 342C, which may be a randomly occurring event or condition. For instance, as shown in FIG. 3C, error event 342C may occur during the execution or scheduling of therapy related task 306B. Error event 342C may correspond to an unexpected occurrence, such as a movement of an electrode (e.g., electrode 128 of FIG. 1), during delivery of high frequency ablation therapy (e.g., RF therapy) to a patient. As another example, error event 342C may correspond to a patient being shorted to ground. In response to detecting error event 342C, the processor may be configured to reschedule tasks that are scheduled to be executed subsequent to the occurrence of error event 342C, to schedule other tasks in time slots occupied by the rescheduled tasks, or both. For instance, as depicted in FIG. 3C, the processor may be configured to schedule safety related task 308C in lieu of time flexible task 308B and may likewise time shift subsequently scheduled tasks as shown in FIG. 3C, while maintaining the periodic schedule of therapy related tasks, such as therapy related task 314B. Additionally or alternatively, the processor may reschedule lower priority tasks, such as time relaxed tasks, during a rescheduling operation, by rescheduling such lower priority tasks to occur during a subsequent high frequency ablation treatment cycle (not depicted).

Figure 4A:
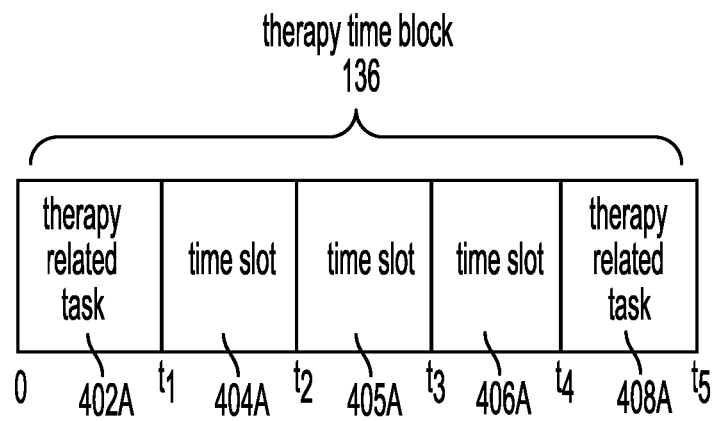
FIGS. 4A and 4B are block diagrams illustrating an example adaptive context sensitive time division multiplexed scheduling operation according to one or more aspects.
Figure 4B:
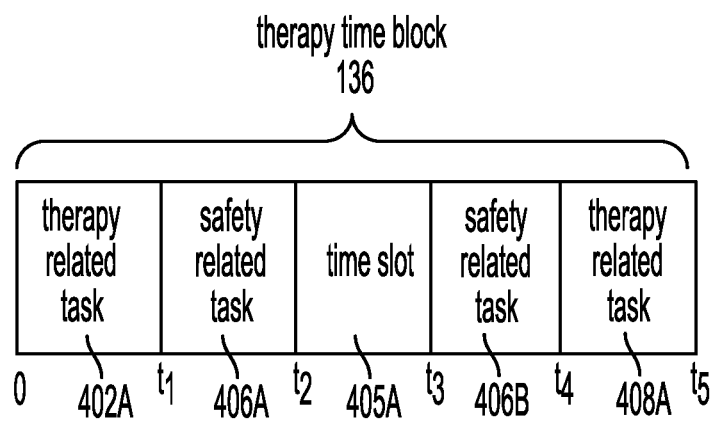

FIGS. 4A and 4B are block diagrams illustrating an example adaptive context sensitive time division multiplexed scheduling operation according to one or more aspects. FIGS. 4A and 4B further illustrate an adaptive scheduling feature of implementations in which a processor (e.g., processor 104 of FIG. 1) may be configured to schedule safety related tasks during available time slots within a therapy time block. In this way, high priority safety related tasks may be executed during delivery of high frequency ablation therapy.

In FIG. 4A, a processor (e.g., processor 104 of FIG. 1) has been configured to schedule therapy related task 402A and therapy related task 408A in time slots of therapy time block 136 in an implementation. The processor may be configured to leave time slots 404A-406A unassigned (i.e., to not schedule tasks in those time slots), because, for example, additional tasks may not be pending scheduling in a scheduling queue. Alternatively or additionally, the processor may be configured to calculate an expected value of a possible safety task that would require scheduling such that if the expected value exceeds a threshold value, the processor is configured to leave time slots 404A-406A unassigned in anticipation of one or more safety tasks pending scheduling in a scheduling queue.

Referring to FIG. 4B and in response to determining that time slots 404A-406A have no corresponding scheduled tasks and that therapy related tasks are not pending scheduling in, for instance, a scheduling queue, the processor may be configured to schedule safety related tasks 406A, 406B in time slots 404A, 406A. Thus, by scheduling safety related tasks during a high frequency ablation therapy cycle, safety related tasks can be performed during a high frequency therapy cycle thereby enhancing an overall operational safety of the high frequency ablation device.

Figure 5A:
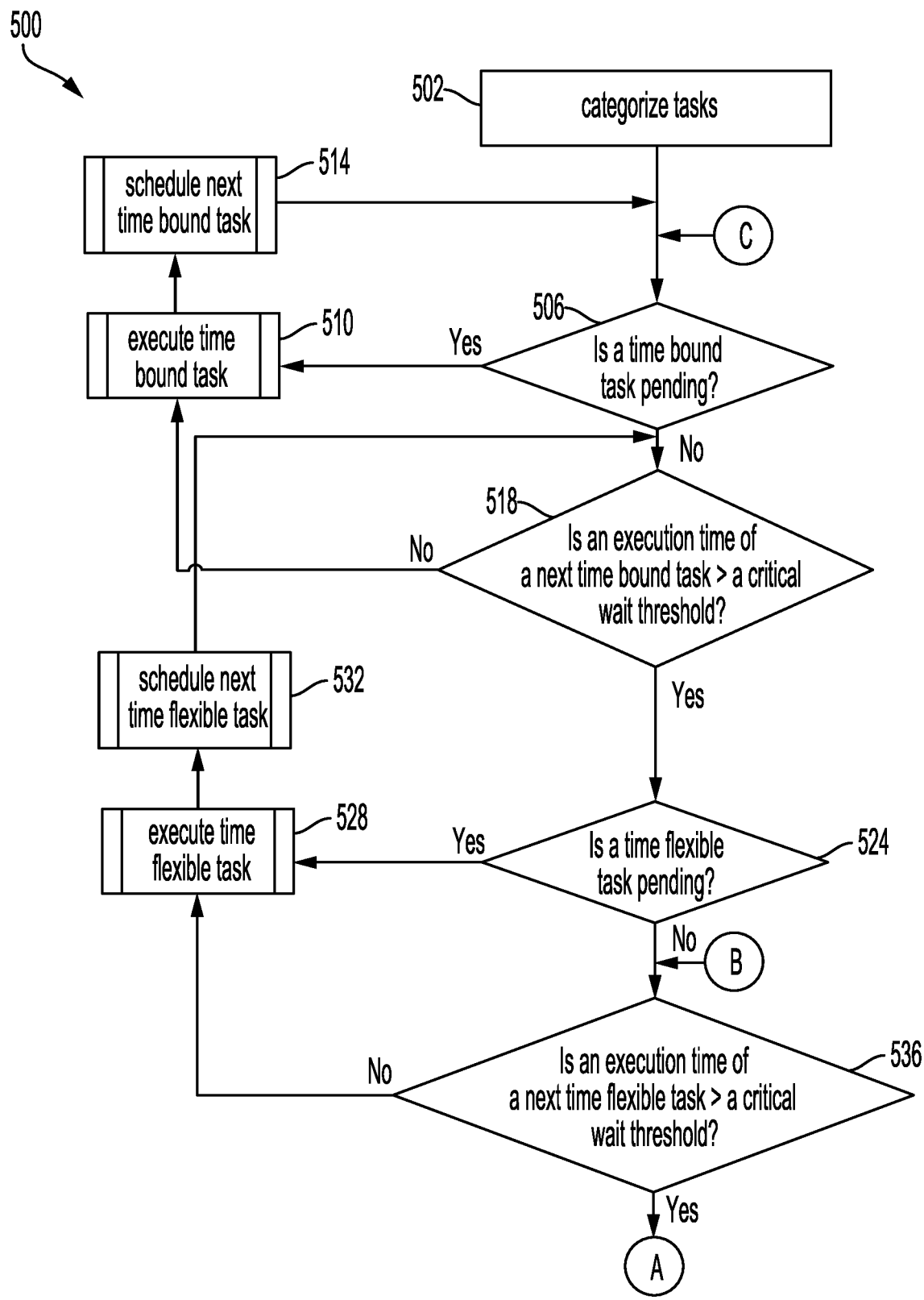
FIGS. 5A and 5B are flow diagrams illustrating an example process that supports adaptive context sensitive time division multiplexed control of a high frequency ablation system according to one or more aspects.
Figure 5B:
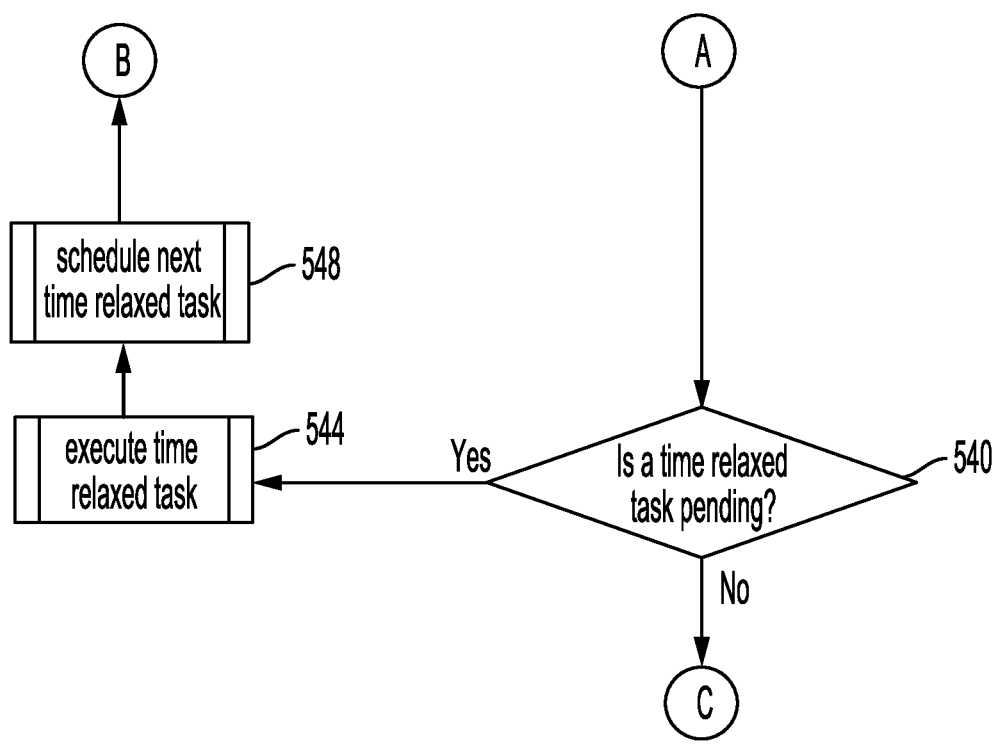

FIGS. 5A and 5B are flow diagrams illustrating an example process 500 that supports adaptive context sensitive time division multiplexed control of a high frequency ablation system according to one or more aspects. At block 502, tasks may be categorized. For example, a processor, such as one or more processors, of the high frequency ablation device may be configured to categorize tasks. Tasks may include instructions that the processor is to execute or that the processor is to cause other components of the high frequency ablation device to execute. In accordance with some examples, tasks may be categorized into a first category that includes time bound tasks, into a second category that includes time flexible tasks, and/or into a third category that includes time relaxed tasks. Tasks falling into the first category may have a higher priority of execution, scheduling, or both than tasks falling into the second category and into the third category. Similarly, tasks failing into the second category may have a higher priority of execution, scheduling, or both than tasks falling in the third category.

Time bound tasks of some embodiments may be tasks that relate to provision of therapy to a patient, such as therapy related tasks and safety related tasks. Therapy related tasks of some embodiments may include tasks directed to controlling a high frequency generator (e.g., an RF generator) of the high frequency ablation device, one or more relays (e.g., switching circuitry) of the high frequency ablation device, one or more electrodes of the high frequency ablation device, or any combination thereof. Examples of therapy related tasks may include controlling the one or more relays (e.g., switching circuitry) of the high frequency ablation device to a particular channel configuration, setting a level of an output voltage produced by the high frequency generator of the high frequency ablation device, monitoring a frequency and a magnitude of current output at a cannula of the high frequency ablation system, or any combination thereof. Examples of safety-related tasks include, in response to determining that an output voltage is outside of acceptable parameters, changing certain inputs to a proportional-integral-derivative (PID) controller to better control the output voltage, sending an alert via one or more input/output devices of the high frequency ablation device to a user of the device to adjust one or more therapy parameters, or any combination thereof.

Time flexible tasks of some examples may be tasks that relate to an overall operational integrity of the high frequency ablation system. Examples of such tasks include reading data from sensors, setting an operational rate (e.g., revolutions per minute (RPM)) of a cooling fan positioned within a housing of the high frequency ablation device, monitoring a temperature within the housing of the high frequency ablation device, and any combination thereof. Time relaxed tasks include latency tolerant tasks that relate to processing inputs received from and outputs sent to input/output devices of the high frequency ablation device.

At block 506, it may be determined whether a time bound task is pending scheduling, execution, or both. For example, a processor of the high frequency ablation device may determine that one or more time bound tasks are pending execution, scheduling, or both in in a scheduling queue or in an execution queue. At block 510, in response to determining that a time bound task is pending execution in the execution queue, the processor of the high frequency ablation device may be configured to execute the time bound task. At block 514 in response to determining that one or more time bound tasks are pending scheduling in the scheduling queue, the processor of the high frequency ablation device may be configured to schedule the one or more time bound tasks. To illustrate, in response to determining that one or more time bound tasks are pending scheduling, the processor may assign time slots within one or more time blocks allocated for time bound tasks (e.g., in a therapy time block) to the one or more time bound tasks. The processor may be configured to execute the scheduled time bound tasks within a timeframe corresponding to the time slot at which the time bound task is scheduled to be executed.

In response to determining, by the processor, that a time bound task is not pending execution, scheduling, or both, (e.g., that there are no time bound tasks waiting to be scheduled in a scheduling queue, to be executed in an execution queue, or both) process 500 may proceed from block 506 to block 518. At block 518, it may be determined whether an execution time of a next scheduled time bound task in an execution queue exceeds a critical wait threshold. In an implementation, a critical wait threshold may be a timeframe value stored in a memory of the high frequency ablation device. A processor of the high frequency ablation device may compare the timeframe value to an amount of time needed to execute a next scheduled time bound task in the execution queue. If the execution time of the next scheduled time bound task in the execution queue does not exceed the critical wait threshold, then process 500 may proceed to block 510 at which the next scheduled time bound task in the execution queue may be executed. However, if the execution time of the next scheduled time bound task exceeds the critical wait threshold, then process 500 may proceed to block 524.

At block 524, it may be determined whether a time flexible task is pending execution, scheduling, or both. For instance, the processor of the high frequency ablation device may determine that one or more time flexible tasks are pending execution, scheduling, or both. In an implementation, in response to determining that a time flexible task is pending execution in an execution queue, the process may proceed from block 524 to block 528. At block 528, the processor of the high frequency ablation device may execute the time flexible task. If one or more time flexible tasks are pending scheduling in a scheduling queue, process 500 may proceed to block 532. At block 532, the processor of the high frequency ablation device may schedule the one or more time flexible tasks in the scheduling queue for execution by allocating a time slot to the one or more time flexible tasks. In an implementation, if a time block allocated for time bound tasks (e.g., a therapy time block) includes unassigned time slots, the processor of the high frequency ablation device may assign time slots within time blocks allocated for time bound tasks to time flexible tasks. Otherwise, if the processor of the high frequency ablation device determines that each time slot within the time block allocated for time bound tasks (e.g., a therapy time block) has been assigned a task, the processor of the high frequency ablation device may assign time slots within system time blocks to the time flexible tasks. Alternatively or additionally, the processor may be configured to first schedule the one or more time flexible tasks in one or more system time blocks before searching for unassigned time slots in the one or more therapy time blocks.

However, in response to determining that a time flexible task is not pending execution, scheduling, or both, process 500 may proceed from block 524 to block 536. At block 536, it may be determined whether an execution time of a next scheduled time flexible task exceeds the critical wait threshold value. If the execution time of the next scheduled time flexible task does not exceed the critical wait threshold value, process 500 may proceed from block 536 to block 528 at which the next scheduled time flexible task in an execution queue is executed. Otherwise, process 500 may proceed from block 536 to block 540 of FIG. 5B. At block 540 of FIG. 5B, it is determined whether a time relaxed task is pending execution, scheduling, or both. If a time relaxed task is not pending execution, scheduling, or both, process 500 may return to block 506 of FIG. 5A, where it is determined (e.g., by a processor of the high frequency ablation device) whether a time bound task is pending scheduling, execution, or both.

Otherwise, process 500 may proceed from block 540 of FIG. 5B to block 544 of FIG. 5B. At block 544, the processor of the high frequency ablation device may execute any time relaxed task pending in an execution queue. If one or more time relaxed tasks are pending scheduling in a scheduling queue, process 500 may proceed to block 548. At block 548, the processor of the high frequency ablation device may schedule the one or more time relaxed tasks that are pending scheduling in the scheduling queue. In an implementation, the processor of the high frequency ablation device may schedule the one or more time relaxed tasks in time slots within system time blocks. Alternatively or additionally, the processor may schedule time relaxed tasks in any available time slots in therapy time blocks. Process 500 may then proceed to block 536 of FIG. 5A, at which it is determined (e.g., by a processor of the high frequency ablation device) whether an execution time of a next scheduled time flexible task is greater than a critical wait threshold.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps. Moreover, the scope of the present application is not intended to be limited to the particular embodiments of the process, machine, manufacture, composition of matter, means, methods and steps described in the specification.

What is claimed is:

1. A method of operating a high frequency ablation device that is configured to provide an ablation therapy to a patient, comprising:
    operating a high frequency generator to generate a high frequency signal; and
    performing switching operations to output the high frequency signal to one or more output channels using time division multiplexing, wherein the time division multiplexing comprises operating one or more processors to:
        (a) categorize multiple system tasks into a plurality of categories, wherein the plurality of categories include a time bound tasks category, having a first priority, a time flexible tasks category having a second priority, and a time relaxed tasks category having a third priority, wherein the first priority is higher than the second priority and the second priority is higher than the third priority;
        (b) allocate, from a time block in which the tasks are to be scheduled, at least first one or more time blocks;
        (c) divide the at least first one or more time blocks into one or more first time slots based, at least in part, on data corresponding to a state of a high frequency ablation system of which the high frequency ablation device is a component; and
        (d) schedule, in the one more first time slots, one or more time bound tasks corresponding to the time bound tasks category.

2. The method of claim 1, wherein the tasks categorized into the time bound tasks category include therapy related tasks, safety related tasks, or both, wherein the tasks categorized into the time flexible tasks category include system related tasks, and the tasks categorized into the time relaxed tasks category include input and output related tasks.

3. The method of claim 1, wherein the time division multiplexing further comprises operating the one or more processors to:
    allocate, from the time block in which the tasks are to be scheduled, second one or more time blocks;
    divide the second one or more time blocks into second one or more time slots based, at least in part, on the data;
    schedule, in the second one or more time slots, one or more time flexible tasks corresponding to the time flexible tasks category, one or more time relaxed tasks corresponding to the time relaxed tasks category, or both; and
    execute, by a first processor of the one more processors, the one or more time bound tasks, one or more time flexible tasks, or both and, by a second processor of the one or more processors, one or more time relaxed tasks.

4. The method of claim 1, wherein categorization of the multiple system tasks into the plurality of categories is configured to facilitate generation of a context sensitive and adaptive schedule of one or more time bound tasks, one or more time flexible tasks, and one or more time relaxed tasks.

5. The method of claim 1, wherein division of the at least first one or more time blocks into one or more first time slots based, at least in part, on the data is configured to facilitate a multiplexed control of the high frequency ablation device.

6. The method of claim 1, wherein one or more time bound tasks of the time bound tasks category are scheduled at periodic time slots selected from among the one or more first time slots, wherein the one or more time bound tasks correspond to therapy related tasks, and wherein scheduling the one or more time bound tasks at the periodic time slots enhances an accuracy and a control of high frequency ablation therapy delivered by the high frequency ablation device.

7. The method of claim 1, wherein the time division multiplexing further comprises operating the one or more processors to:
    determine that insufficient time bound tasks are in a queue to allocate to each of the one or more first time slots; and
    schedule, in the one more first time slots, one or more time flexible tasks, one or more time relaxed tasks, or both in response to the determination that insufficient time bound tasks are in the queue.

8. The method of claim 1, wherein the time division multiplexing further comprises operating the one or more processors to:

detect, based on input received from one or more sensors of the high frequency ablation device, an error event; and schedule, in a time slot of the one or more first time slots, one or more time bound tasks, wherein the one or more time bound tasks include at least one safety related task.

9. The method of claim 1, wherein the data comprises at least first data indicative of a physical state of a high frequency ablation system, and wherein the physical state of the high frequency ablation system includes at least one of a quantity of electrodes coupled to relays of the high frequency ablation device, a configuration of the electrodes of the high frequency ablation device, and a presence of a ground pad within the high frequency ablation device.

10. The method of claim 9, wherein the data further comprises second data indicative of an operational state of the high frequency ablation system, and wherein the operational state of the high frequency ablation system includes at least one of a polarity of operation of the high frequency ablation system and a therapy state of the high frequency ablation system.

11. The method of claim 1, wherein the tasks of the time bound tasks category include therapy related tasks, and in which the therapy related tasks include configuring the one or more processors to:

controllably connect relays of the high frequency ablation device to a particular channel configuration;

set a level of an output voltage of a radio frequency (RF) generator of the high frequency ablation device; and measure a therapy related characteristic of the high frequency ablation device, wherein the therapy related characteristic includes an output voltage of the RF generator, an output current of the RF generator, or both.

12. The method of claim 1, wherein time bound tasks of the time bound tasks category include safety related tasks, and wherein the safety related tasks include operating the one or more processors to cause one or more sensors of the high frequency ablation device to measure fluctuations in an operating power of the high frequency ablation device.

13. The method of claim 1, wherein time flexible tasks of the time flexible tasks category include system related tasks, and wherein the system related tasks include operating the one or more processors to:

monitor sensor data received from sensors of the high frequency ablation device;

monitor one or more error lines of the high frequency ablation device; and set a temperature threshold associated with an ambient temperature within a housing of the high frequency ablation device.

14. The method of claim 1, wherein time relaxed tasks of the time relaxed task category include input and output related tasks, and wherein the input and output related tasks include operating the one or more processors to regulate input received at and output generated by one or more user interfaces of the high frequency ablation device.

* * * * *